United States Patent
Elschenbroich

(10) Patent No.: US 9,456,761 B2
(45) Date of Patent: Oct. 4, 2016

(54) CURRENT PROTECTION FOR ELECTRODE-BASED MONITORING SYSTEMS

(75) Inventor: Rainer Willi Elschenbroich, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 136 days.

(21) Appl. No.: 14/003,246

(22) PCT Filed: Mar. 6, 2012

(86) PCT No.: PCT/IB2012/051043
§ 371 (c)(1),
(2), (4) Date: Sep. 5, 2013

(87) PCT Pub. No.: WO2012/120445
PCT Pub. Date: Sep. 13, 2012

(65) Prior Publication Data
US 2013/0345535 A1    Dec. 26, 2013

(30) Foreign Application Priority Data
Mar. 10, 2011 (EP) ..................... 11157654

(51) Int. Cl.
*A61B 5/0424* (2006.01)
*A61B 5/0428* (2006.01)

(52) U.S. Cl.
CPC ......... *A61B 5/0424* (2013.01); *A61B 5/04282* (2013.01); *A61B 2560/045* (2013.01); *A61B 2562/222* (2013.01); *A61B 2562/227* (2013.01)

(58) Field of Classification Search
CPC ............ A61N 1/08; A61N 2001/086; A61N 2001/14; A61N 2001/15; A61N 2001/37; A61N 2001/3718; A61B 5/04004; A61B 5/0424; A61B 5/0428; A61B 5/04282; A61B 5/04284; A61B 5/04286
USPC ..................... 600/393, 508; 607/63
See application file for complete search history.

(56) References Cited

U.S. PATENT DOCUMENTS

| | | | |
|---|---|---|---|
| 4,038,990 A | | 8/1977 | Thompson |
| 4,164,215 A | * | 8/1979 | Finlayson et al. ............ 600/508 |
| 5,217,010 A | | 6/1993 | Tsitlik et al. |
| 6,246,902 B1 | | 6/2001 | Naylor et al. |
| 7,822,484 B1 | * | 10/2010 | Zhao et al. ................... 607/116 |
| 2002/0079910 A1 | * | 6/2002 | Fukuda ........................ 324/692 |
| 2004/0049242 A1 | * | 3/2004 | Ibrahim ......................... 607/57 |
| 2007/0073175 A1 | | 3/2007 | McAtamney et al. |
| 2009/0149920 A1 | | 6/2009 | Li et al. |
| 2009/0171421 A1 | * | 7/2009 | Atalar et al. .................... 607/63 |

* cited by examiner

*Primary Examiner* — Eugene Wu

(57) ABSTRACT

When applying shielded ECG leads to a patient, during the presence of strong RF signals such as electrocautery, high currents may flow through the cable capacitance to the shield and from there back to the patient via another cable capacitance and electrode, thus causing skin burnings. Such high currents can be reduced dramatically when the shields of the lead cable are separated by means of connecting series resistances into the shield conductors. Implementing these resistors into a ECG trunk cable allows the usage of uniform lead cables for all applications.

8 Claims, 1 Drawing Sheet ated by the the lead shield, the first shield and the
CURRENT PROTECTION FOR ELECTRODE-BASED MONITORING SYSTEMS

FIELD OF THE INVENTION

The present invention relates to an apparatus for protecting patients connected to electrode-based monitoring systems, such as electrocardiogram (ECG) devices, against excessive current which, for example, may be caused by electrocautery applications.

BACKGROUND OF THE INVENTION

During monitoring of ECG signals, surgeons often use electrocautery devices. Electrocautery is a surgical technique which involves introducing high frequency current to a specific area of the body in order to remove unwanted tissue, seal off blood vessels, or to create a surgical incision. The instrument used to perform electrocautery is also known as an electrocautery. An electrocautery uses a high frequency, usually upwards of 100 kHz, to ensure that the patient's nerves and muscles are not stimulated. Lower frequencies could cause twitching and cramps, which would be a serious problem. Depending on the voltage used, the electrocautery can have varying effects on the patient's body. Thus, a very high level of radio frequency energy is coupled to the patient and in consequence to the inputs of the monitor.

Many implementations for reducing the amount of RF energy have been suggested, e.g. in U.S. Pat. No. 4,038,990, where coupled inductances are used together with capacitors, or in U.S. Pat. No. 5,217,010, where various LC filter alternatives are presented.

However, these known implementations do not consider the issue of RF currents which are carried by a separate shield. Especially, in ECG applications with shielded lead sets which are exposed to electrocautery RF energy, the problem arises that a current path is provided through the cable capacitance (inner conductor to shield). Thus, when all shields are connected together, a high current may flow through the series connection of these cable capacities, thus causing skin burnings at the electrode sites at the patient.

To reduce the risk for these burnings, it has been suggested reducing the current flowing into the lead wires by applying series protection elements in form of impedances (R and/or L) directly into the grabber of the lead set. However, a big disadvantage is that for a monitoring of respiration signals, which imply a low-impedance path to the patient, the ECG lead sets with built-in protection elements have to be replaced by such without protection elements. This is time-consuming and circumstantial, so it is highly desirable to avoid this procedure.

In U.S. Pat. No. 6,246,902 protection elements are no longer provided in the lead cable and the shields of the lead cable set are separated. Putting the protection elements in a separate block allows the usage of uniform unshielded lead sets for both operating and intensive care units. The shield conductors can also be fed through the block in a separated manner. Furthermore, in the shield conductors an inductance may be inserted to prevent current from flowing through the series connection of cable capacitances and in addition obtaining RF blocking in the shield while maintaining a good conductivity for low frequencies which obviously was the goal of this implementation.

However, the method of using inductors for separating and filtering shields has the disadvantages that the inductors are big and expensive and behave like capacitances above their resonance frequency. Thus, at higher frequencies they are again a good conductor. The fact that electrocautery frequencies are in the range of several hundred kHz up to 4 MHz makes it difficult to find an adequate inductor with a sufficient inductance to suppress the RF signals while its resonance frequency is still low enough. Moreover, together with (parasitic) capacitances, resonances can occur which degrade the RF suppression capability. Especially when there is a series resonance of the cable capacitance with the inductor, the currents can increase to an amount where burnings may occur again. Hence, especially when using lead cables of different length—or even unshielded lead cables—it is very difficult to assure that no resonance will occur at any condition.

In US 2009/149920 A1 a method is provided of using a resistive shield covering the lead of a pacemaker in order to avoid RF energy pickup during MRI procedures. The implementation of a costly and complicated resistive shield is only suitable if energy pickup is to be avoided over the whole length of the lead.

SUMMARY OF THE INVENTION

It is an object of the present invention to provide a more effective way of separating the shields to prevent excessive shield currents.

This object is achieved by an apparatus as claimed in claim 1.

Accordingly, a resistor is connected in series to the first shield(s), i.e. between the first shield and the second shield or between the first shield and the lead shield, so as to attenuate a current flowing through a conductor path generated by the the lead shield, the first shield and the (common) second shield. Thereby, an effective solution for current protection is provided by using (the) resistor(s) in the shield conductors instead of inductors. This is possible due to the fact that the AC impedance of the coupling capacity to low frequency interference sources, such as 50/60 Hz sources or electrostatic discharge sources, is very much higher than the resistance which can be used here for an effective reduction of the undesired currents. Thus, the influence of these interferences on the ECG signal quality will be negligible, and, for the purpose of electrostatic discharge protection the additional resistor(s) will not degrade the performance, because the source impedance of static charges at the lead cable is even much higher than the AC coupling impedances.

The proposed solution provides the advantages that resistors are cheap and small, so that they can be easily integrated into existing monitoring systems. Furthermore, RF energy is simply changed into heat and no resonances can occur. Moreover, present resonances due to (parasitic or intended) inductances (Ls) and capacitances (Cs) can be damped. This may even lead to a further reduction of interference at the patient monitor. Thus, at all lead cable lengths (i.e. lead cable capacitances), patient burnings at electrode sites can be prevented because there is no series resonance.

According to a first aspect, the apparatus may comprise a plurality of the first signal conductors each having an input end adapted for coupling to a respective one of a plurality of the lead wires each connecting to a respective one of a plurality of the physiological signal sensors, and each of the plurality of first signal conductors having an output end adapted for coupling to a respective one of a plurality of the second signal conductors, the apparatus further comprising a plurality of the first shields positioned for shielding the first signal conductors, and the apparatus further comprising a plurality of the resistors each connected between a respective one of the plurality of first shields and a respective one of a plurality of the second shields positioned for shielding the plurality of lead wires or between a respective one of the plurality of first shields and the second shield arranged as a common shield positioned for shielding all of the plurality of second signal conductors, so as to attenuate currents flowing through conductor paths generated by the plurality of lead shields, the plurality of first shields and the second shield. Thus, an arrangement with a plurality of sensors and shielded sensor wires can be protected at a centralized location where the wires are bundled and provided with a common shield.

According to a second aspect which can be combined with the first aspect, a (plurality of) interference filter circuit(s) may be connected between a respective one of the first signal conductors and a respective one of the plurality of the second signal conductor(s). Thereby, additional interference protection can be provided.

According to a third aspect which can be combined with the first or second aspect, the apparatus may be arranged as a trunk block having an input connecting portion for connecting the plurality of lead wires and the plurality of lead shields, and having an output connecting portion consisting of the plurality of second signal conductors and the second shield. The third aspect provides an advantageous modular arrangement which can be interconnected so as to enhance conventional monitoring systems. The third aspect can be modified by providing an additional single output cable containing the common shield and the plurality of second signal conductors, the single cable having a first end connected to the trunk block and an opposite second end connected to a multi-pin connector including the output connecting portion for connecting a socket or jack of the patient monitor.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

In the following embodiment, an enhanced protection against excessive shield currents for patient monitoring devices, such as ECG devices, is described.

According to the embodiment, shield cable currents can be reduced dramatically when the shields of the lead cable are separated by connecting at least one series resistance into or to the shield conductor(s). These resistors may for example be provided in an ECG trunk cable to allow the usage of uniform lead cables for all applications.

Usually, the coupling capacitance of the lead cable to 50/60 Hz sources is in the range of some picofarads (pF). Under extreme circumstances, it could increase to about 100 pF.

This results in a coupling impedance which will be in the range of some 1000 MΩ, under extreme circumstances it could decrease to about 30 MΩ. Compared with these values, a resistance of e.g. 10 kΩ will decrease a common mode signal of 100 V and 30 MΩ source impedance—which is an absolute worst case—to only 0.03 V, under normal conditions even to 0.001 V.

Typically, conventional systems provide a common mode rejection of more than 90 dB. Thus, a 0.03 V root mean square (RMS) signal is reduced to less than 3 µVpp (peak-to-peak voltage) which is much less than the normal noise of an ECG (the Association for the Advancement of Medical Instrumentation (AAMI) requires 30 µVpp). A signal of 0.001 V, as it occurs under normal circumstances, will even be reduced to 0.1 µVpp. The fact that the patient himself has usually a tighter coupling to interference sources than the lead cable supports the fact that a very low impedance shielding of the leads is not necessary, because the patient will introduce much more noise into the system than the cable will.

For the purpose of electrostatic discharge protection the additional resistor also will not degrade the performance, because the source impedance of static charges at the lead cable is even much higher than the AC coupling impedances mentioned above.

The implementation is done by designing a new ECG trunk cable and/or trunk block, in which all shields are put together behind the resistor. Thus, it has the advantage that no insertable filters can get lost—the trunk cable simply always remains with the particular monitor.

Figure 1:
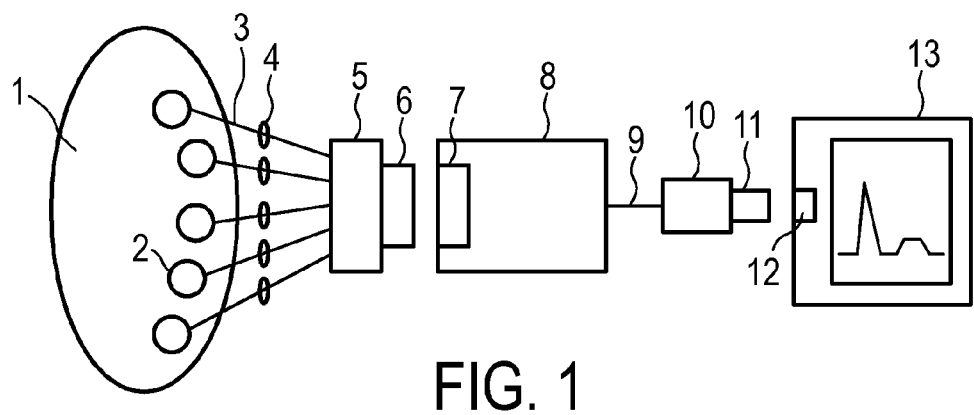
FIG. 1 shows schematic block diagram of a monitoring system according to the preferred embodiment.

FIG. 1 shows a schematic block diagram of a monitoring system according to the preferred embodiment. A plurality of ECG electrodes 2 or other types of physiological signal sensors are attached to the body of a patient 1 so as to acquire physiological signals from the patient 1. Multiple lead wires 3 with respective electromagnetic shields 4 positioned for shielding the lead wires 3 are connected at one end to respective ones of the electrodes 2 and at the other end to a lead connector 5. The lead connector 5 has a connecting end 6 which can be plugged into a socket or jack 7 of a trunk block 8 with protection circuitry 8 (not shown in FIG. 1). From the trunk block 8, a single trunk cable 9 with a common shield leads to a trunk connector 10 with a multi-pin connecting end 11 which can be plugged into a socket or jack 12 connected to a physiological signal processing circuit (not shown) of a patient monitor 13. Thereby, a modular system can be provided, wherein the trunk block 8 or the lead connector 5 can be modified to provide the enhanced protection against excessive shield currents.

Figure 2:
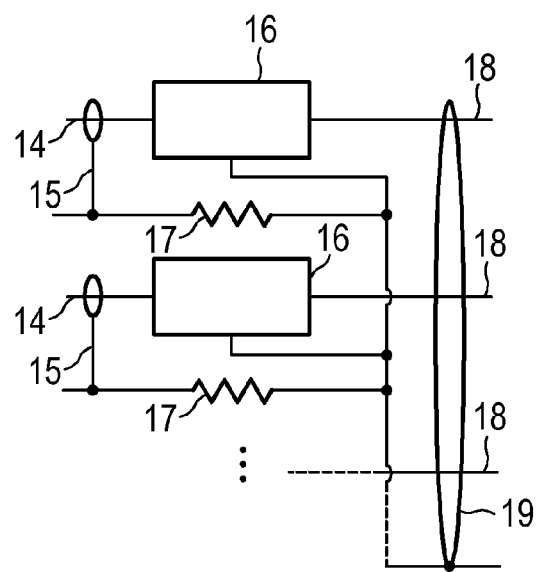
FIG. 2 shows a schematic circuit diagram of a protection circuit according to the preferred embodiment.

FIG. 2 shows a schematic circuit diagram of the protection circuitry in the trunk block 8. The protection circuitry contains an interference filter 16 which can be any kind of RLC filter (or a subset of it). Additionally, electromagnetic shields 15 positioned for shielding the ECG signal conductors 14 are combined behind respective protective resistors 17. The signal conductors 14 and the electromagnetic shields 15 in the trunk block 8 are connected via the lead connector 5 of FIG. 1 to the external lead wires 3 and the external electromagnetic shields 4, respectively. ECG signal conductors 18 behind the filter have a common shield 19 and can be arranged as the trunk cable 9 of FIG. 1.

According to an exemplary implementation of the protection circuitry according to the embodiment, the interference filter 16 may be a serial connection of a resistor (e.g. 10 kΩ) and an inductor (e.g. 6.8 mH). The protective resistors 17 may be implemented with a value of e.g. 22 kΩ, for example. Of course, other values can be selected depending on the desired application.

As an alternative, the protective resistors 17 could as well be integrated in the connecting end 6 of the lead connector 5 or in the connecting jack 7 of the trunk block 8.

In summary, when applying shielded ECG leads to a patient, during the presence of strong RF signals such as electrocautery, high currents may flow through the cable capacitance to the shield and from there back to the patient via another cable capacitance and electrode, thus causing skin burnings. Such high currents can be reduced dramatically when the shields of the lead cable are separated by means of connecting series resistances into the shield conductors. Implementing these resistors into an ECG trunk cable allows the usage of uniform lead cables for all applications.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, sensing unit or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope thereof.

When applying shielded ECG leads to a patient, during the presence of strong RF signals such as electrocautery, high currents may flow through the cable capacitance to the shield and from there back to the patient via another cable capacitance and electrode, thus causing skin burnings. Such high currents can be reduced dramatically when the shields of the lead cable are separated by means of connecting series resistances into the shield conductors. Implementing these resistors into a ECG trunk cable allows the usage of uniform lead cables for all applications.

The invention claimed is:

1. An apparatus for coupling physiological signals acquired from a patient to a physiological processing circuit in a patient monitor, the apparatus comprising:
   a plurality of first ECG signal conductors each first ECG signal conductor having an input end configured to be coupled to a respective one of a plurality of lead wires, each lead wire being configured to connect to a respective one of a plurality of physiological signal sensors, and each of said plurality of first ECG signal conductors having an output end configured to be coupled to a respective one of a plurality of second ECG signal conductors configured to connect with the patient monitor;
   a plurality of electromagnetic shields, each of the plurality of shields being configured and disposed to electromagnetically shield a corresponding one of the first ECG signal conductors;
   a common shield configured to shield all of the plurality of second ECG signal conductors;
   a plurality of ohmic resistors configured to resistively interconnect the plurality of electromagnetic shields with each other and with the common shield, the plurality of ohmic resistors being connected with the electromagnetic shields such that all of the electromagnetic shields are resistively interconnected such that currents flowing from any one of the electromagnetic shields to any other of the electromagnetic shields are attenuated by at least one of the ohmic resistors and the plurality of ohmic resistors being connected between each of the electromagnetic shields and the common shield such that currents flowing between any one of the electromagnetic shields and the common shield are attenuated by at least one of the ohmic resistors.

2. The apparatus according to claim 1, further including:
   each lead wire of the plurality of lead wires being shielded by a corresponding lead shield;
   a connector assembly configured to connect each of the plurality of lead wires and corresponding lead shield to a corresponding one of the first ECG signal conductors and the electromagnetic shields.

3. The apparatus according to claim 1, further including:
   a trunk cable including the plurality of second ECG signal conductors and the common shield.

4. The apparatus according to claim 1, further including:
   a plurality of interference filters, the lead wires being connected with the first ECG signal conductors by the interference filters.

5. An apparatus for coupling physiological signals acquired from a patient to a physiological processing circuit in a patient monitor, the apparatus comprising:
   a plurality of ECG electrodes;
   a plurality of ECG leads, each lead including a lead conductor shielded by a corresponding lead shield;
   a plurality of ECG signal conductors configured to conduct ECG signals;
   a plurality of electromagnetic shields, each electromagnetic shield being configured and disposed to electromagnetically shield a corresponding one of the ECG signal conductors;
   a connector assembly configured to connect each of the lead conductors to a corresponding one of the ECG signal conductors and connect each lead shield to a corresponding one of the electromagnetic shields;
   a trunk cable including a plurality of cable conductors and a common shield, the common shield being configured to shield the plurality of cable conductors, the cable conductors being connected with corresponding ECG signal conductors; and
   a plurality of ohmic resistors electrically connecting the electromagnetic shields with each other via at least one of the ohmic resistors to resistively interconnect all of the electromagnetic shields, and electrically connecting the electromagnetic shields with the common shield via at least one of the ohmic resistors to resistively interconnect the electromagnetic shields and the common shield.

6. An apparatus for coupling physiological signals acquired from a patient to a physiological signal processing circuit in a patient monitor, said apparatus comprising:
   a) a plurality of first signal conductors each having an input end coupled to a respective one of a plurality of lead wires, each lead wire connecting to a respective one of a plurality of physiological signal sensors, and each of said plurality of first signal conductors having an output end coupled to a respective one of a plurality of second signal conductors which connect with the patient monitor;
   b) a plurality of first shields, each of the plurality of first shields shielding one of said first signal conductors;
   c) a second shield arranged as a common shield shielding all of said plurality of second signal conductors; and
   d) a trunk block including:

an input connecting portion configured to connect to said plurality of lead wires and said plurality of first shields, an output connecting portion configured to connect with the second signal conductors and the second shield, and a plurality of resistors each connected between a respective one of said first shields and said second shield, the plurality of resistors being connected to the first shields such that currents flowing between said plurality of first shields and said second shield flow through the plurality of resistors and are attenuated.

7. The apparatus according to claim 6, further comprising:
a single cable containing said common shield and said plurality of second signal conductors, said-single cable having a first end connected to the output connecting portion of said trunk block and an opposite second end configured to be plugged into a jack or socket.

8. The apparatus according to claim 6, further comprising:
a plurality of interference filter circuits each connected between a respective one of said first signal conductors and a respective one of said plurality of second signal conductors.

* * * * *